United States Patent
Milliman et al.

(10) Patent No.: US 8,109,426 B2
(45) Date of Patent: Feb. 7, 2012

(54) SURGICAL TILT ANVIL ASSEMBLY

(75) Inventors: Keith L. Milliman, Bethel, CT (US);
Thomas Wenchell, Durham, CT (US);
Philip C. Roy, Orange, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 201 days.

(21) Appl. No.: 12/512,342

(22) Filed: Jul. 30, 2009

(65) Prior Publication Data
US 2010/0038401 A1 Feb. 18, 2010

Related U.S. Application Data

(60) Provisional application No. 61/088,055, filed on Aug. 12, 2008.

(51) Int. Cl.
*A61B 17/115* (2006.01)
(52) U.S. Cl. ........................ 227/175.1; 227/19
(58) Field of Classification Search .... 227/175.1–182.1, 227/19
See application file for complete search history.

(56) References Cited

U.S. PATENT DOCUMENTS

| | | | |
|---|---|---|---|
| 5,344,059 A * | 9/1994 | Green et al. | 227/179.1 |
| 5,588,579 A | 12/1996 | Schnut et al. | |
| 5,639,008 A | 6/1997 | Gallagher et al. | |
| 5,758,814 A | 6/1998 | Gallagher et al. | |
| 5,860,581 A * | 1/1999 | Robertson et al. | 227/179.1 |
| 6,053,390 A * | 4/2000 | Green et al. | 227/179.1 |
| 6,945,444 B2 | 9/2005 | Gresham et al. | |
| 6,957,758 B2 | 10/2005 | Aranyi | |
| 7,168,604 B2 * | 1/2007 | Milliman et al. | 227/176.1 |
| 7,179,267 B2 * | 2/2007 | Nolan et al. | 606/153 |
| 7,234,624 B2 | 6/2007 | Gresham et al. | |
| 7,303,106 B2 * | 12/2007 | Milliman et al. | 227/175.1 |
| 7,325,713 B2 | 2/2008 | Aranyi | |
| 7,364,060 B2 * | 4/2008 | Milliman | 227/175.1 |
| 7,431,191 B2 | 10/2008 | Milliman | |
| 7,494,038 B2 * | 2/2009 | Milliman | 227/179.1 |
| 7,516,877 B2 | 4/2009 | Aranyi | |
| 7,546,940 B2 | 6/2009 | Milliman et al. | |
| 7,556,186 B2 | 7/2009 | Milliman | |
| 7,942,302 B2 * | 5/2011 | Roby et al. | 227/175.1 |
| 2004/0087977 A1 | 5/2004 | Nolan et al. | |
| 2004/0195289 A1 | 10/2004 | Aranyi | |
| 2005/0023325 A1 | 2/2005 | Gresham et al. | |
| 2005/0205639 A1 * | 9/2005 | Milliman | 227/175.1 |
| 2006/0097025 A1 * | 5/2006 | Milliman et al. | 227/175.1 |

(Continued)

FOREIGN PATENT DOCUMENTS

| | | |
|---|---|---|
| EP | 0570915 A2 | 11/1993 |
| EP | 1658813 A1 | 5/2006 |
| EP | 1857058 A1 | 11/2007 |
| EP | 2042108 | 4/2009 |

OTHER PUBLICATIONS

US 5,826,777, 10/1998, Green et al. (withdrawn)

*Primary Examiner* — Rinaldi Rada
*Assistant Examiner* — Andrew M Tecco

(57) ABSTRACT

A surgical tilt anvil assembly including a rod and a head assembly including an anvil plate having staple deforming pockets. The head assembly is pivotally secured to the rod and pivotal in relation to the rod between a first tilted position, a non-tilted position and a second different tilted position. The head assembly passes from the first tilted position, through the non-tilted position to the second tilted position.

8 Claims, 15 Drawing Sheets

U.S. PATENT DOCUMENTS

| | | |
|---|---|---|
| 2006/0229643 A1 | 10/2006 | Nolan et al. |
| 2007/0060952 A1 | 3/2007 | Roby et al. |
| 2007/0075117 A1* | 4/2007 | Milliman et al. ........... 227/179.1 |
| 2007/0078486 A1* | 4/2007 | Milliman et al. .............. 606/219 |
| 2007/0181632 A1* | 8/2007 | Milliman ................... 227/179.1 |
| 2007/0272722 A1 | 11/2007 | Aranyi |
| 2008/0230581 A1* | 9/2008 | Marczyk et al. ........... 227/176.1 |
| 2009/0179063 A1 | 7/2009 | Milliman et al. |
| 2009/0250502 A1 | 10/2009 | Milliman |

\* cited by examiner

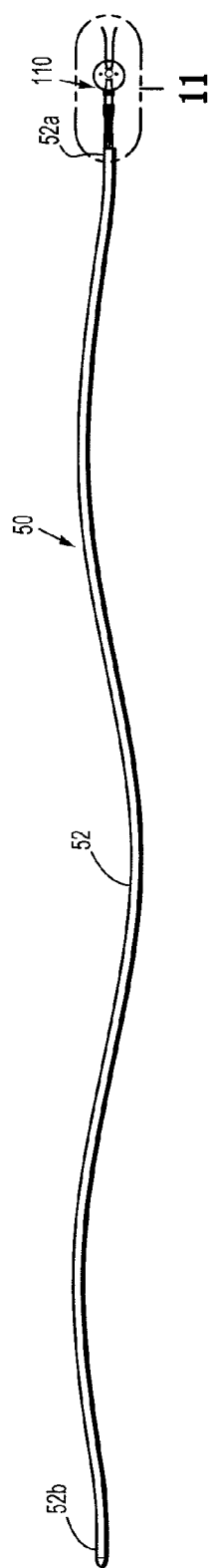
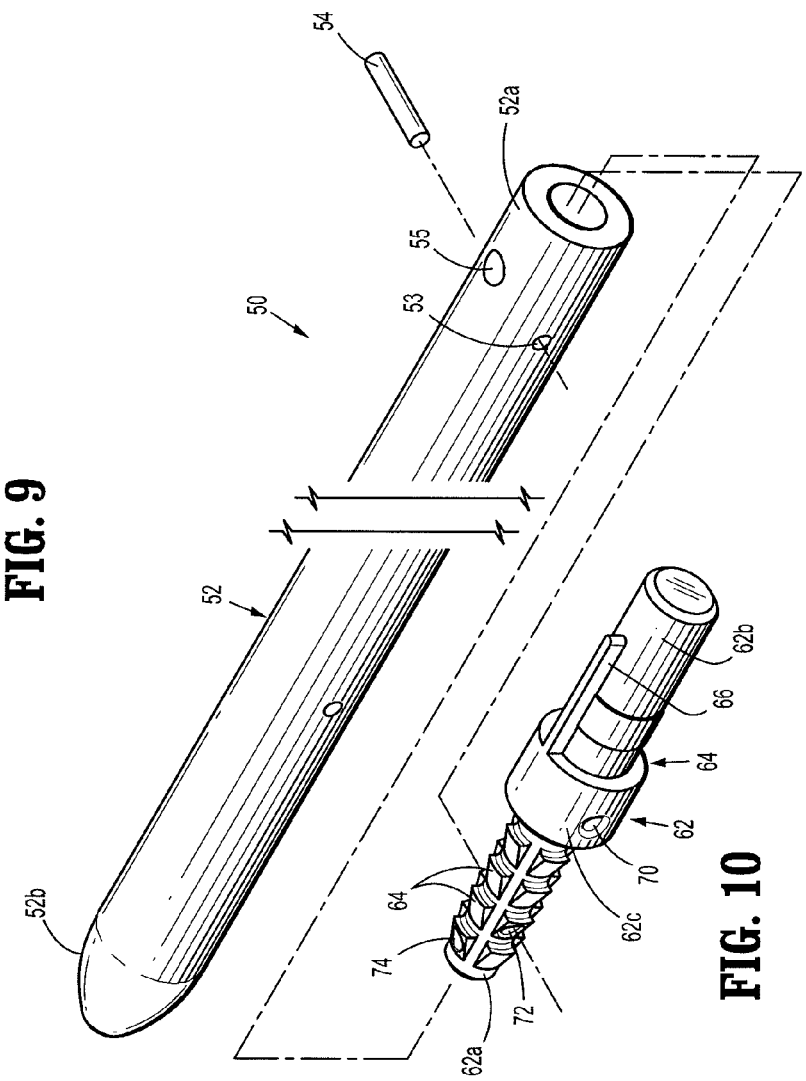
FIG. 9
FIG. 10

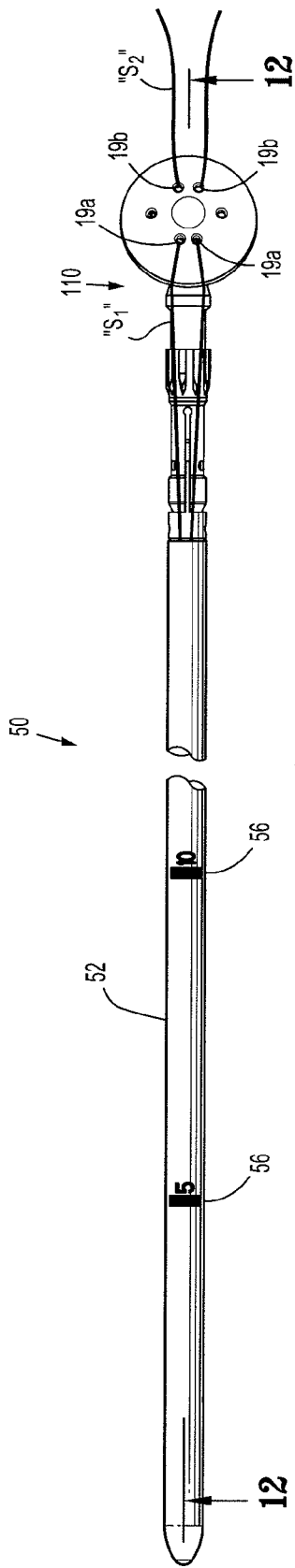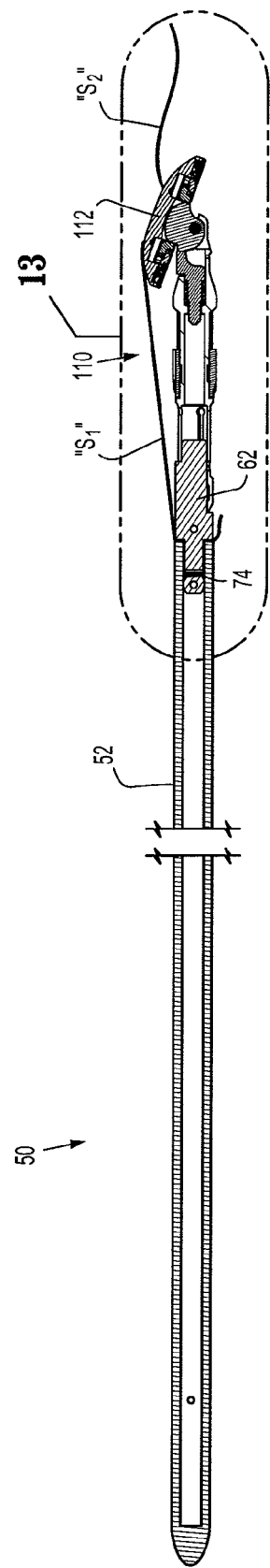
FIG. 11
FIG. 12

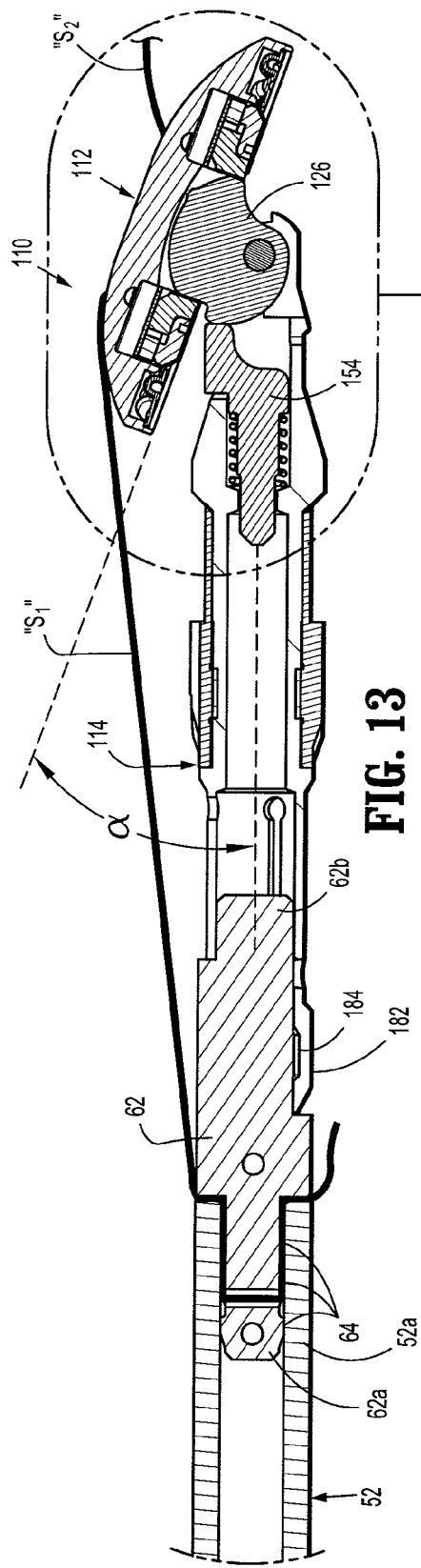
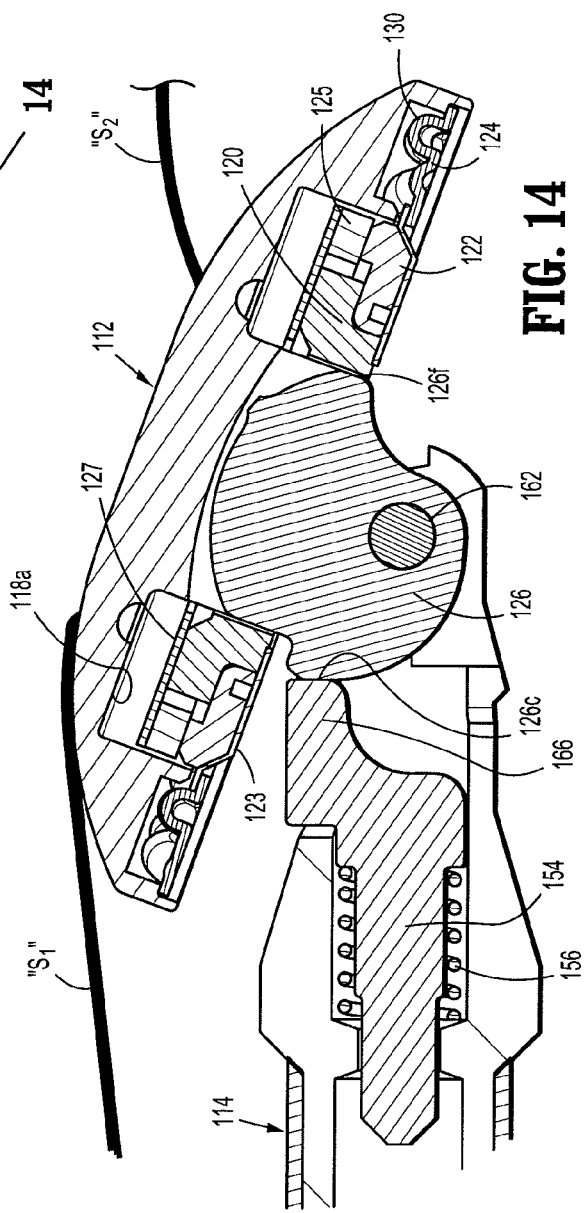
FIG. 13
FIG. 14

SURGICAL TILT ANVIL ASSEMBLY

CROSS REFERENCE TO RELATED APPLICATION

The present application claims the benefit of and priority to U.S. Provisional Application Ser. No. 61/088,055 filed on Aug. 12, 2008, the entire contents of which are incorporated herein by reference.

BACKGROUND

1. Technical Field

The present disclosure relates generally to an anvil assembly which is suitable for use with a circular anastomosis stapler. More specifically, the present disclosure relates to an anvil assembly having a tiltable head which is suitable for use with a circular anastomosis stapler.

2. Background of Related Art

Circular anastomosis staplers which include an anvil assembly having a tiltable anvil head are known in the art. U.S. Pat. No. 6,053,390 discloses an anvil assembly having an anvil head that is tilted. A linkage system for tilting the anvil assembly of a surgical stapler from a tilted to a non-tilted position during approximation and back to a tilted position upon return of the anvil to a spaced position is disclosed in U.S. Pat. No. 6,957,758. Other anvil assemblies which pivot from a tilted position to an operative position upon approximation of the anvil assembly and then return to the tilted position upon firing of the stapler are also known and are described in U.S. Pat. Nos. 7,168,604 and 7,431,191. Another tilt anvil assembly is disclosed in U.S. Patent Publication 2008-0230581. Although the ability of the anvil head to be delivered in the tilted reduced profile position and tilt once the anvil is attached to an instrument and subsequently approximated to an operative position for firing of the staples has advantages, it would be desirable provide a tilted anvil of simplified design and increased controllability.

SUMMARY

A surgical tilt anvil assembly is provided. The tilt anvil assembly includes in one aspect a rod and a head assembly including an anvil plate having staple deforming pockets. The head assembly is pivotally secured to the rod and pivotal in relation to the rod between a first tilted position, a non-tilted operative position and a second different tilted position, wherein the head assembly passes from the first tilted position, through the non-tilted position to the second tilted position.

The head assembly can include a backup member movable about a post from a first position in which the backup member is positioned to prevent pivotal movement of the head assembly from the non-tilted position to the second tilted position, to a second position in which the backup member is positioned to permit pivotal movement of the head assembly in relation to the rod from the non-tilted position to the second tilted position.

The head assembly of the tilt anvil assembly may further include a pivotal cam latch member positioned to engage the backup member to prevent movement of the backup member from the second position to the first position. The head assembly may be pivotally secured to the rod about a pivot member, and a pivotal latch member may be pivotally mounted about the pivot member. The latch member may be positioned to engage an inner periphery of the backup member when the backup member is in its first position. The latch member may include a curved surface which is configured to eliminate any gap between the latch member and the backup member during movement of the head assembly from the first position to the second position.

The tilt anvil assembly may further include a plunger which is urged by a biasing member into engagement with the cam latch member to urge the cam latch member to its pivoted position. The tilt anvil assembly may further include a retainer member positioned in the head assembly to prevent movement of the backup member from the first position to the second position until a predetermined force has been applied to the backup member. The retainer member may include a deformable member which is positioned in the head assembly between the housing and the backup member. The housing and the post may define an annular recess, and the retainer member can be positioned in the annular recess. The retainer member may include an annular body positioned about the post and a plurality of deformable tabs extending therefrom.

The backup member can be positioned to abut the retainer member such that upon movement of the backup member from its first position to its second position, the deformable tabs are deformed. The backup member may include a cutting ring and a backup plate, and the cutting ring can be secured to a proximal face of the backup plate. The backup plate may include at least one finger positioned to engage a surface of the rod when the backup member is in its first position to prevent pivotal movement of the head assembly in relation to the rod. The cutting ring may be formed from a softer material than the backup plate. The rod may define a longitudinal axis and a pivot axis of the head assembly can intersect the longitudinal axis of the center rod.

In a preferred embodiment, the head assembly is maintained in a first tilted position by a tensioning member connected to the head assembly. In a preferred embodiment, the tensioning member is a suture received in an opening in the head assembly. A second suture can be provided in a second opening in the head assembly extending in a direction opposite the first suture for retrieval of the anvil assembly.

In another aspect of the disclosure a surgical tilt anvil assembly is provided including a rod and an anvil head assembly pivotally secured to the rod and pivotal in relation to the rod in a first direction from a first tilted position for insertion to an operative position, and further pivotal in relation to the rod in the first direction from the operative position to a second tilted position for removal.

The head assembly in a preferred embodiment moves through an arc of about 140 degrees from the first tilted position to the second tilted position. The head assembly may further include a pivotal latch member positioned to prevent movement of a backup member of the head assembly from a second position to an initial position. A plunger in a preferred embodiment moves the head assembly from the first tilted position to the operative position and from the operative position to the second tilted position. In a preferred embodiment, a suture maintains the head assembly in the first tilted position.

In another aspect of the present disclosure, a surgical anvil assembly is provided comprising a rod and a head assembly including a housing, a cam member and a backup member. The head assembly is pivotally secured to the rod and pivotal in relation to the rod in a first direction from a first tilted position for insertion to an operative position, and further pivotal in relation to the rod from the operative position to a second tilted position different from the first tilted position. The cam member prevents proximal movement of the backup member after the backup member is advanced distally. The anvil assembly can further include a plunger spring biased into engagement with the cam member.

In another aspect of the present disclosure a surgical anvil delivery system is provided comprising an anvil assembly including a rod and a head assembly, a flexible tube and a tensioning member. The head assembly is pivotally secured to the rod and movable from a first tilted position to a non-tilted operative position. The anvil assembly is connected to the flexible tube and the tensioning member is connected to the head assembly and maintains the head assembly in the first tilted position such that release of the tensioning member returns the head assembly to the non-tilted position. In a preferred embodiment, the tensioning member is a suture extending through a hole in the head assembly and into an opening in the flexible tube. The system may further include a second suture connected to the head assembly and extending in a direction different than the first suture.

In a preferred embodiment, the head assembly is further pivotable to a second tilted position after positioning in the operative non-tilted position, wherein the second tilted position is different than the first tilted position. The anvil assembly may further include a rotatable cam member and a plunger spring biased into contact with the cam member, wherein the cam member is rotatable and the plunger is movable distally to move the head assembly from the first tilted position to the operative position and further movable to move the head assembly from the operative position to a second different tilted. An adapter can be provided to connect the anvil assembly to the flexible tube.

In another aspect, the present disclosure provides a method for pivoting an anvil head assembly of a surgical anvil assembly comprising the steps of:

providing an anvil assembly including a rod and a head assembly pivotally secured to the rod, the head assembly movable from a first tilted position to a non-tilted operative position, the anvil assembly connected to a flexible tube and retained in a first tilted position by a tensioning member;

inserting the anvil assembly into a patient with the anvil held in the first tilted position by the tensioning member; and severing the tensioning member to cause the head assembly to move in a first direction to return to the non-tilted operative position.

BRIEF DESCRIPTION OF THE DRAWINGS

Various embodiments of the presently disclosed tilt anvil assembly are disclosed herein with reference to the drawings wherein:

FIG. 9 is a top view of the anvil assembly of FIGS. 1-4 supported on an anvil delivery system;

FIG. 10 is an enlarged exploded view of the anvil delivery system of FIG. 9;

FIG. 11 an enlarged top view of the anvil delivery system of FIGS. 9 and 10, including the anvil assembly of FIGS. 1-4 shown in the first tilted position tensioned by the suture;

FIG. 12 is a cross-sectional side view of the anvil assembly and anvil delivery system of FIG. 11 taken along lines 12-12 of FIG. 11;

FIG. 13 is a cross sectional side view (showing the area of detail of FIG. 12) of the anvil assembly of FIGS. 1-4, in a pre-fired tilted position supported on the anvil delivery system of FIG. 9;

FIG. 14 is an enlarged view of portion 14 of FIG. 13;

DETAILED DESCRIPTION OF EMBODIMENTS

Figure 1:
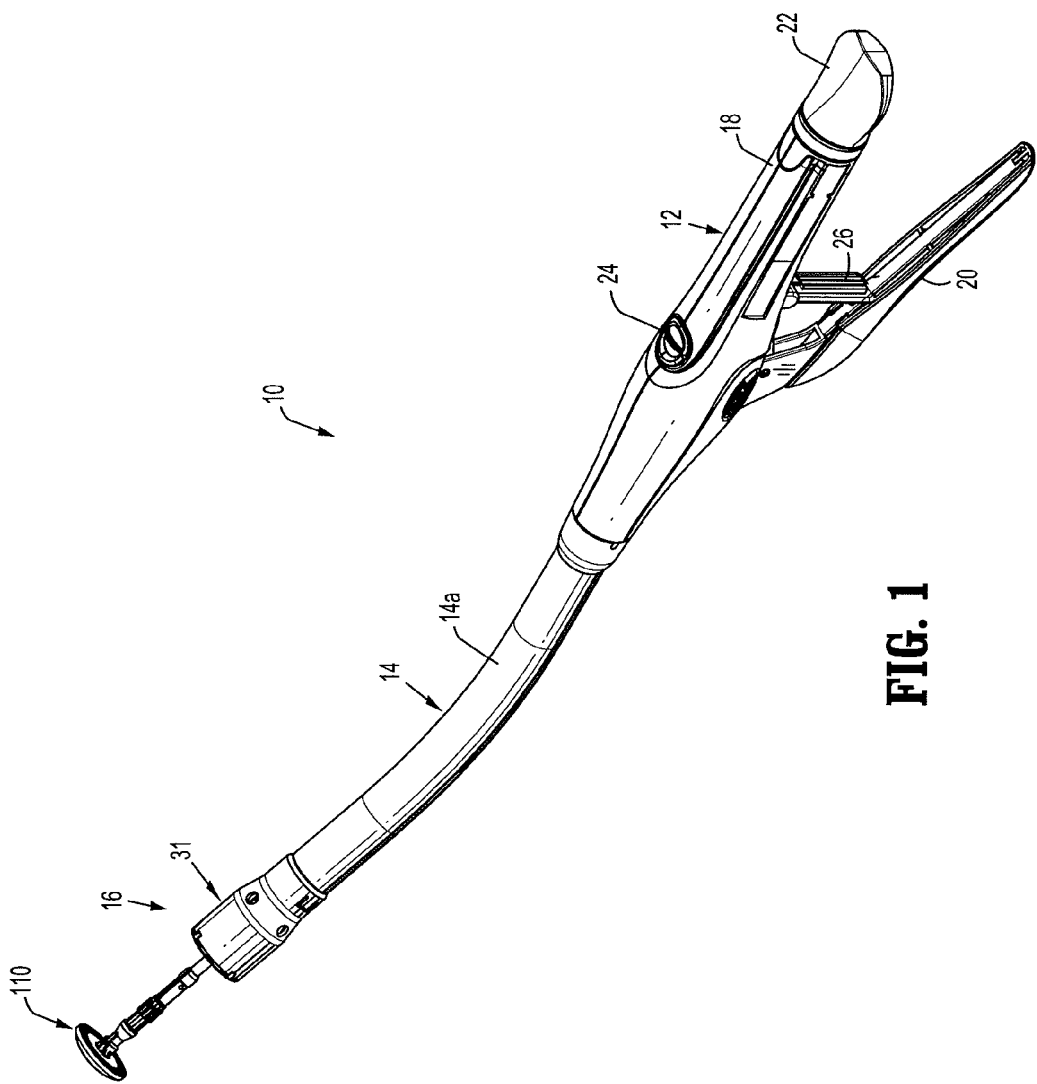
FIG. 1 is a perspective view of a surgical stapling device including an embodiment of an anvil assembly according to the present disclosure.
Figure 2:
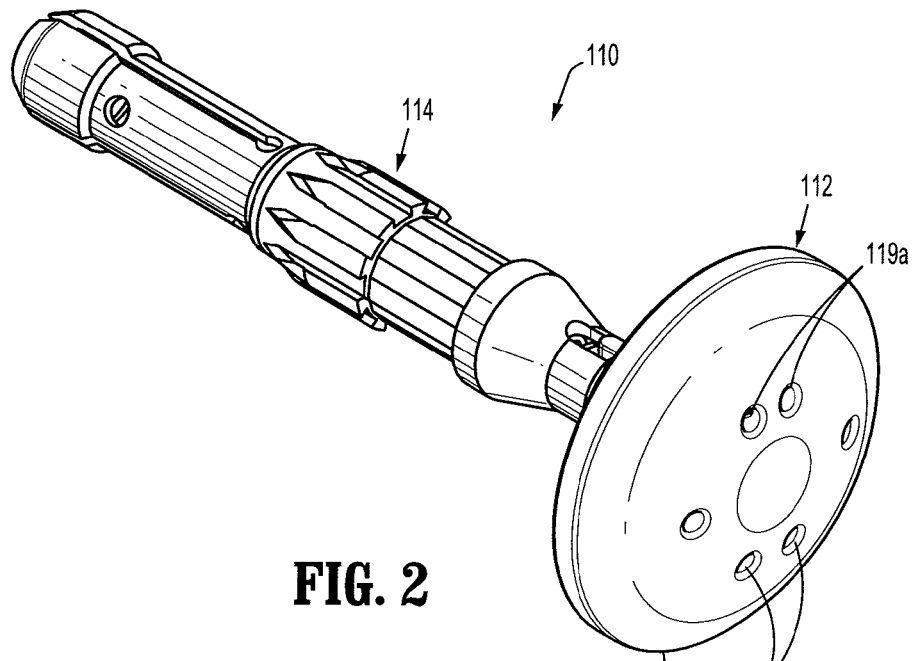
FIG. 2 is a first perspective side view of the anvil assembly of FIG. 1 in the non-tilted position.

Embodiments of the presently disclosed anvil assembly will now be described in detail with reference to the drawings in which like reference numerals designate identical or corresponding elements in each of the several views. Throughout this description, the term "proximal" will refer to the portion of the instrument closer to the operator and the term "distal" will refer to the portion of the instrument further from the operator.

FIG. 1 illustrates an embodiment of a surgical stapling device configured for use with a tilt anvil assembly according to the present disclosure. Briefly, surgical stapling device 10 includes a proximal handle assembly 12, an elongated central body portion 14 including a curved elongated outer tube 14a, and a distal head portion 16. Alternately, in some surgical procedures, e.g., the treatment of hemorrhoids, it is desirable to have a substantially straight, shortened, central body portion. The length, shape and/or the diameter of body portion 14 and distal head portion 16 may also be varied to suit a particular surgical procedure.

With reference still to FIG. 1, handle assembly 12 includes a stationary handle 18, a firing trigger 20, a rotatable approximation knob 22 and an indicator 24. A pivotally mounted trigger lock 26 is fastened to handle assembly 12 and is manually positioned to prevent inadvertent firing of stapling device 10. Indicator 24 is positioned on the stationary handle 18 and includes indicia, e.g., color coding, alpha-numeric labeling, etc., to identify to a surgeon whether the device is approximated and is ready to be fired. Head portion 16 includes an anvil assembly 110 and a shell assembly 31. A more detailed discussion of surgical stapler 10 is disclosed in U.S. Pat. Nos. 7,364,060 and 7,303,106, the contents of which are incorporated herein by reference in its entirety.

Referring now to FIGS. 2-7, an embodiment of the anvil assembly of the present disclosure is shown generally as reference numeral 110. Anvil assembly 110 is shown in a non-tilted or operative position wherein the staple deforming pockets 130 face the staple slots of the instrument. Anvil assembly 110 includes a head assembly 112 and a center rod assembly 114. Head assembly 112 includes a post 116, a housing 118, a backup member or plate 120, a cutting ring 122, a cutting ring cover 123, an anvil plate 124, a spacer or washer 125, a cam latch member 126, and a retainer member 127. Post 116 is monolithically formed with and centrally positioned within housing 118. Alternately, housing 118 and post 116 may be formed separately and fastened together using a known fastening technique, e.g., welding.

As will be discussed in further detail below, housing 118 includes openings 119a, 119b sized and dimensioned to receive one or more sutures "S". During use, a first suture "$S_1$" (FIG. 11) is inserted through openings 119a and is used to retain head assembly 112 in a retracted or first tilted position (FIGS. 11 and 12) during insertion of anvil assembly 110 within a patient. That is, suture "$S_1$" operates as a tensioning member to maintain the head assembly in the first tilted position. A second suture "$S_2$" is inserted through openings 119b and is configured to permit retrieval of tilt anvil assembly 110 from within a patient if desired. During trans-oral insertion of anvil assembly 110, suture "$S_2$" extends from the mouth of patient, permitting the anvil assembly 110 to be retrieved trans-orally. As shown, second suture "$S_2$" extends in a direction opposite the direction of suture "$S_1$".

With reference still to FIGS. 2-7, anvil plate 124 is supported in an outer annular recess 128 of housing 118 and includes a plurality of staple deforming pockets 130 for receiving and deforming staples. At least one tab 124a extends radially outwardly from anvil plate 124 and is received within a cutout 132 formed in an outer rim of housing 118. Tab 124a and cutout 132 function to align or properly position anvil plate 124 within annular recess 128 of housing 118.

Figure 4:
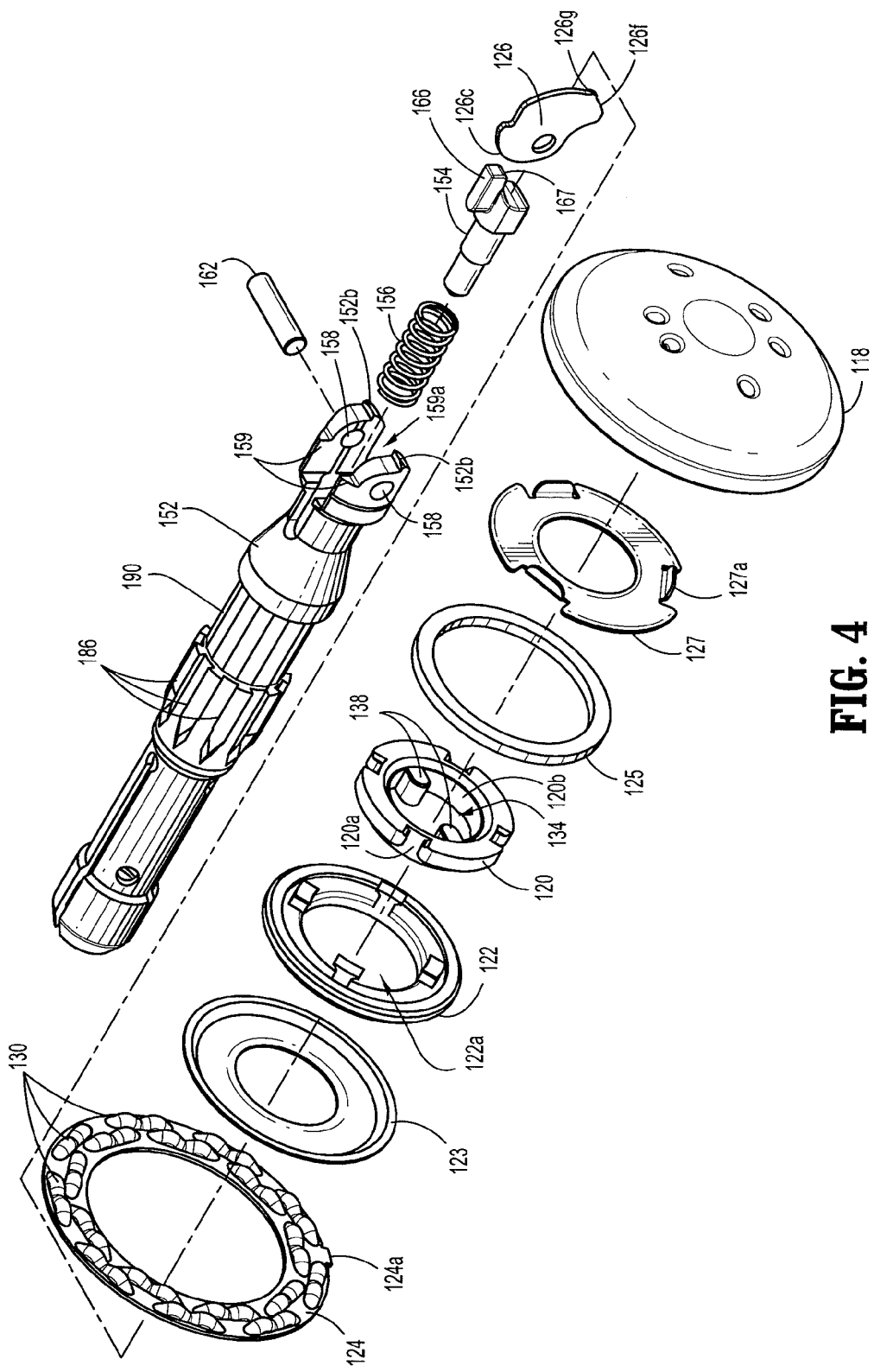
FIG. 4 is an exploded side view of the anvil assembly of FIGS. 1-3.
Figure 7:
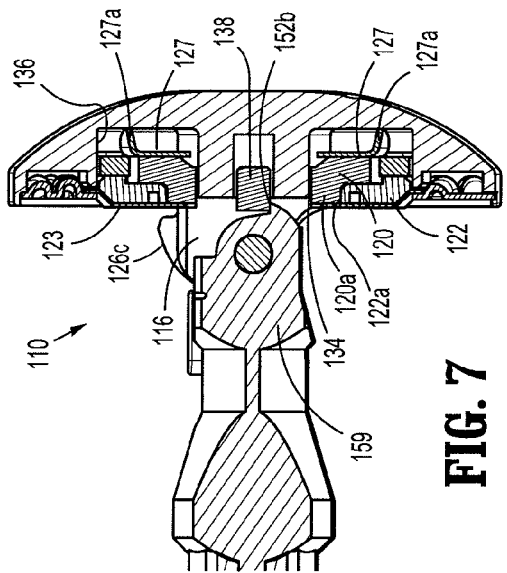
FIG. 7 is a cross-sectional side view of a distal end of the anvil assembly of FIGS. 1-6 taken along line 7-7 of FIG. 5 and showing the head assembly in the non-tilted operative position.
Figure 6:
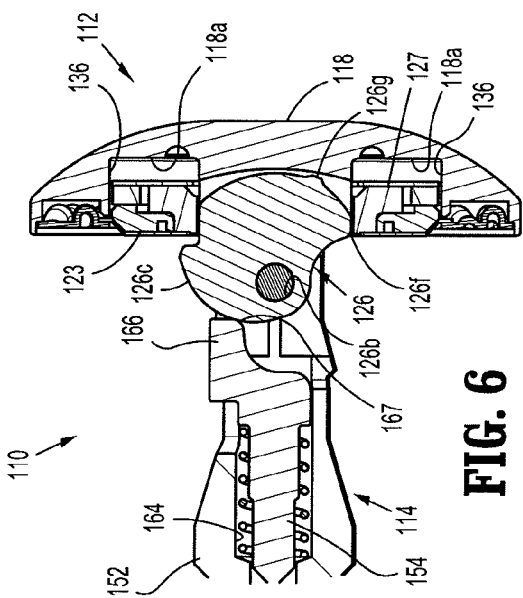
FIG. 6 is a cross-sectional side view of a distal end of the tilt anvil assembly of FIGS. 1-4 taken along line 6-6 of FIG. 5 and showing the head assembly in the non-tilted operative position.
Figure 5:
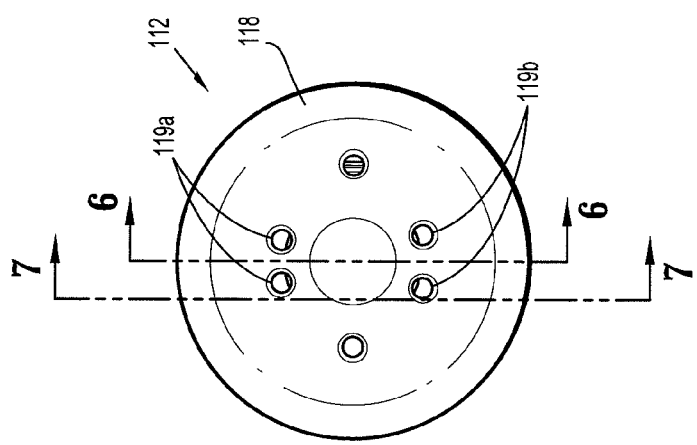
FIG. 5 is an end view of the anvil assembly of FIGS. 1-3.

With particular reference to FIGS. 4, 6 and 7, head assembly 112 will be described in detail. Backup plate 120 includes a central opening 134 which is positioned about post 116 within an inner annular recess 136 of housing 118 between post 116 and outer annular recess 128. Backup plate 120 includes a raised platform 120a. Cutting ring 122 includes an opening 122a having a configuration substantially the same as platform 120a. Although platform 120a is illustrated as having a circular shape, other configurations are envisioned, e.g., square, rectangular, triangular, etc. In one embodiment, cutting ring 122 is formed from polyethylene and is fixedly secured to backup plate 120 using, for example, an adhesive, to form a backup plate/cutting ring assembly. Backup plate 120 is formed from a hard material, e.g., a metal. Alternately other materials of construction may be used to construct backup plate 120 and cutting ring 122. Further, backup plate 120 and cutting ring 122, in the alternative, can be formed as a single or unitary structure.

Still referring to FIGS. 6 and 7, a cutting ring cover 123 is secured to an outwardly facing or proximal surface of cutting ring 122 using, for example, an adhesive. In one embodiment, cutting ring cover 123 is formed from a material or materials, which have a hardness greater than that of the cutting ring, e.g., mylar. In one embodiment, cutting ring cover 123 includes two layers of mylar (not shown) which are joined together using an adhesive and a polypropylene coating. Alternately, cutting ring 122 need not have a cover. Cutting ring 122 and backup plate 120 are slidably mounted about post 116. Backup plate 120 includes a pair of inwardly extending fingers 138 which will be described in further detail below.

With reference still to FIGS. 4, 6 and 7, retainer member 127 is positioned in inner annular recess 136 between backup plate 120 and a back wall 118a of housing 118. In one embodiment, retainer member 127 is annular and includes a plurality of deformable tabs 127a which engage a rear surface of backup plate 120. Retainer member 127 prevents backup plate 120 and cutting ring 122 from moving or being pushed into inner annular recess 136 of housing 118 until a predetermined force sufficient to deform tabs 127a has been applied to the backup plate/cutting ring assembly. The predetermined force can be close to but is less than the force applied by an annular cutting blade of a surgical stapling device when it engages, for example, the cutting ring of anvil assembly 110. In one embodiment by way of example, the predetermined force is between about ten pounds and about ninety pounds and can be about thirty (30) pounds. When the predetermined force is reached, e.g., during cutting of tissue, backup plate 120 is urged into inner annular recess 136 and compresses retainer member 127. It is envisioned that other crushable, deformable, collapsible or movement restricting members may be used to retain the backup plate/cutting ring assembly in a fixed position until a predetermined force has been applied to the backup plate/cutting ring assembly.

As illustrated in FIG. 4, anvil center rod assembly 114 includes a center rod 152, a plunger 154 and plunger spring 156. A first end of center rod 152 includes a pair of arms 159 which define a cavity 159a. Each arm 159 has a transverse throughbore 158 which is aligned with a central longitudinal axis of center rod 152. Alternately, throughbores 158 can be offset from the longitudinal axis of center rod 152. Post 116 of anvil head assembly 112 is dimensioned to be positioned within cavity 159a and also includes a transverse throughbore (not shown). A pivot member 162 pivotally secures post 116 to center rod 152 via the throughbores such that anvil head assembly 112 may be pivotally mounted to anvil center rod assembly 114.

Figure 3:
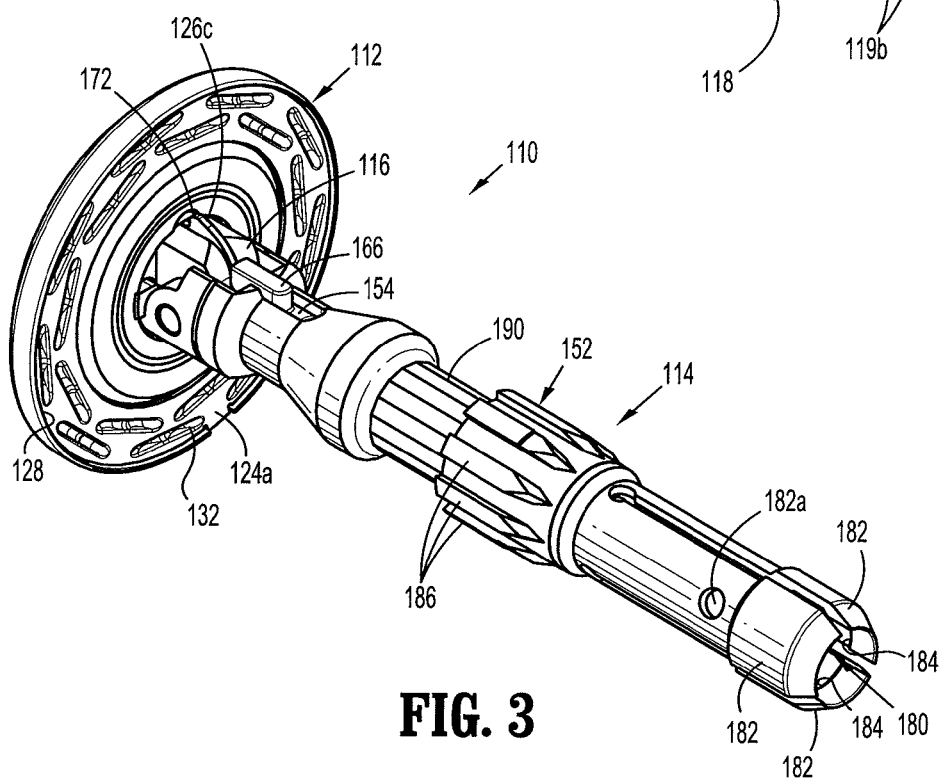
FIG. 3 is a second perspective side view of the anvil assembly shown in FIGS. 1 and 2.
Figure 8:
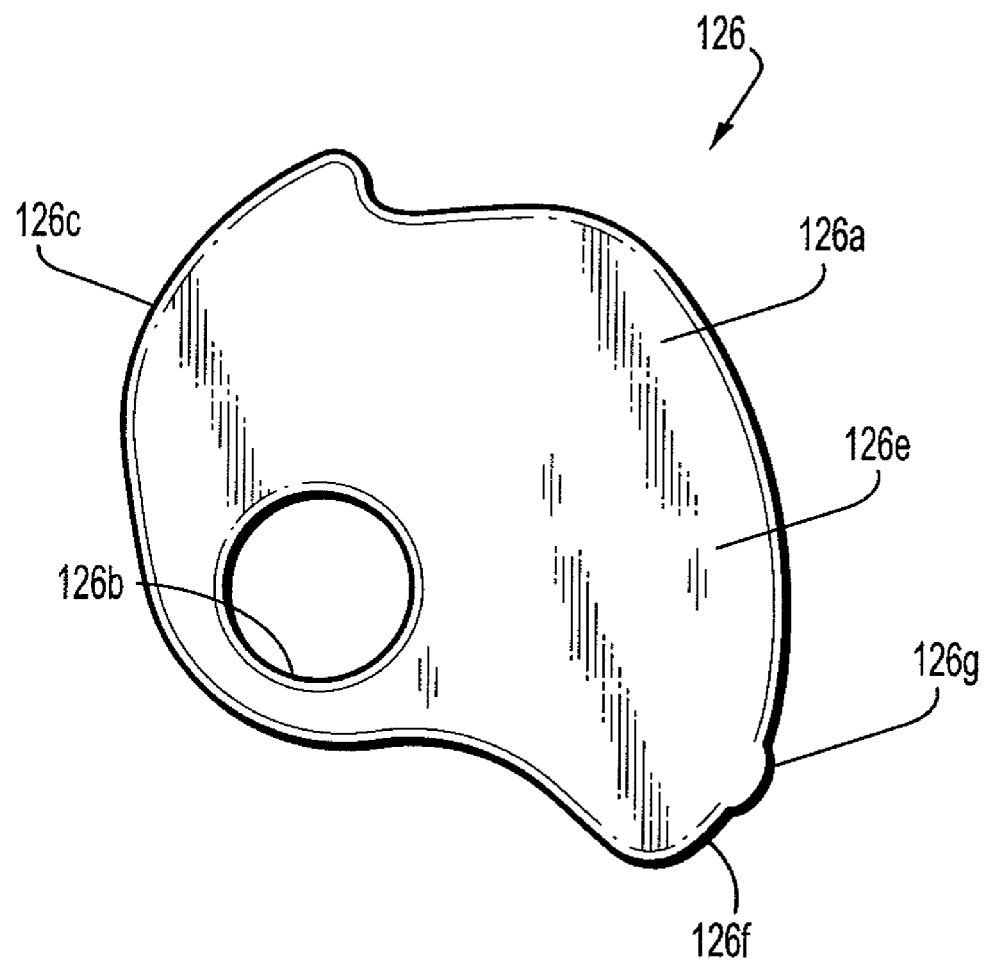
FIG. 8 is an enlarged side view of the cam latch member of the anvil assembly of FIGS. 1-4.

Turning briefly to FIG. 8, cam latch member 126 includes a body 126a having a throughbore 126b. Throughbore 126b is dimensioned to receive pivot member 162 such that cam latch member 126 is pivotally mounted within transverse slot 172 (FIG. 3) of post 116 about pivot member 162. Referring now to FIGS. 3, 6 and 7, cam latch member 126 includes a first body portion 126c which extends partially from slot 172 of post 116 and is positioned to be engaged by a finger 166 of plunger 154. First body portion 126c is configured such that the distance between the surface of first body portion 126c and throughbore 126b increase in a clockwise direction about cam latch member 126. In this manner, plunger 154 is able to move forward as cam latch member 126 rotates in a clockwise direction. Additionally, this configuration of first body portion 126c permits plunger 154 to be retracted as cam latch member rotates in a counter-clockwise direction. Cam latch member 126 also includes an edge 126f, including a tab 126g. A leading portion of edge 126f is configured to be urged into engagement with an inner periphery 120b of backup plate 120 by an engagement finger 166 of plunger 154 when anvil head 112 is in its non-tilted or operative position. Tab 126g is configured to engage backwall 118a of housing 118 to prevent cam latch member 126 from rotating counter-clockwise relative to housing 118.

With reference to FIG. 6, plunger 154 is slidably positioned in a bore 164 formed in the first end of center rod 152. Plunger 154 includes an engagement finger 166 which is offset from the pivot axis of anvil head assembly 112 and biased into engagement with edge 126c of cam latch 126. Engagement of finger 166 with edge 126c of cam latch 126 presses a leading portion of edge 126f against an inner periphery of back plate 120 to urge anvil head assembly 112 to an operative or non-tilted position on center rod 152. In this non-tilted position, finger 166 remains spaced proximally from post 116 of anvil assembly 110.

Turning to FIG. 7, in the pre-fired operative position of head assembly 112, i.e. when head assembly 112 has been pivoted to its non-tilted position, fingers 138 formed on backup plate 120 engage protrusions 152b adjacent top surface 152a of center rod 152 to prevent head assembly 112 from pivoting about pivot member 162.

Anvil head assembly 112 may be tilted a degrees (FIG. 13) relative to anvil center rod assembly 114 to the pre-fired first tilted position by the suture "$S_1$" as described below for insertion. In one embodiment, anvil head assembly 112 is tilted less than ninety degrees and preferably about seventy degrees (70°) in its pre-fired tilted position; however it should be understood that tilting head assembly 112 to other degrees is also contemplated. Titling of anvil head assembly 112 relative to anvil center rod assembly 114 by the suture S1 causes cam latch member 126 positioned within the inner periphery of the backup plate 120 to rotate, causing body portion 126c of cam latch member 126 to engage finger 166 of plunger 154. As cam latch assembly 126 rotates counter-clockwise (as viewed in FIG. 14) with the tilting of anvil head assembly 112, plunger 154 is retracted within bore 164 of anvil center rod assembly 114, thereby compressing spring 156. In this manner, finger 166 of plunger 154 is distally biased against body portion 126c of cam latch member 126.

Figure 18:
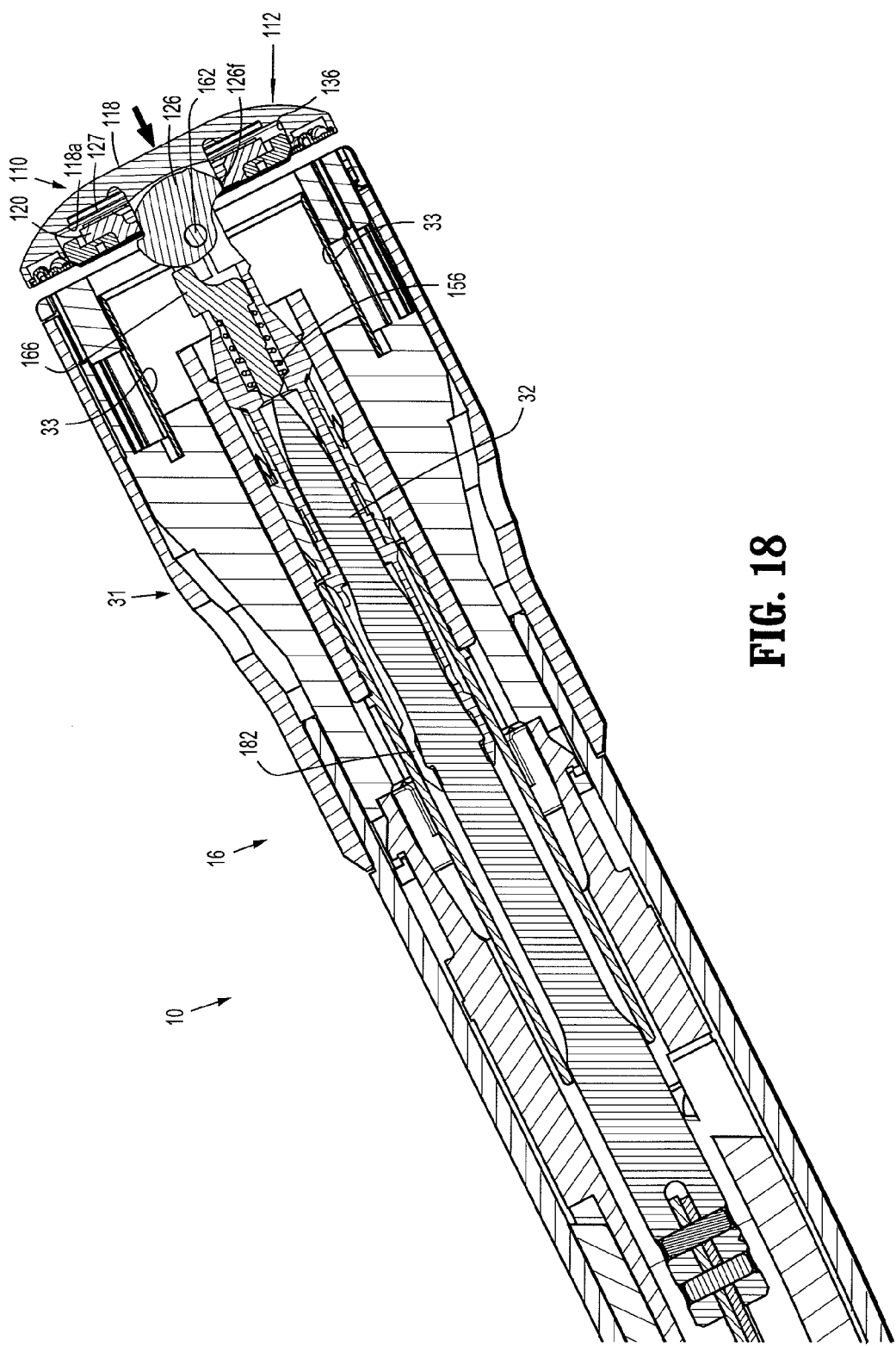
FIG. 18 is an enlarged cross-sectional side view of the distal head portion of the surgical stapling device of FIG. 1, including the connected anvil assembly of FIGS. 1-4 shown in an approximated pre-fired non-tilted operative position.
Figure 19:
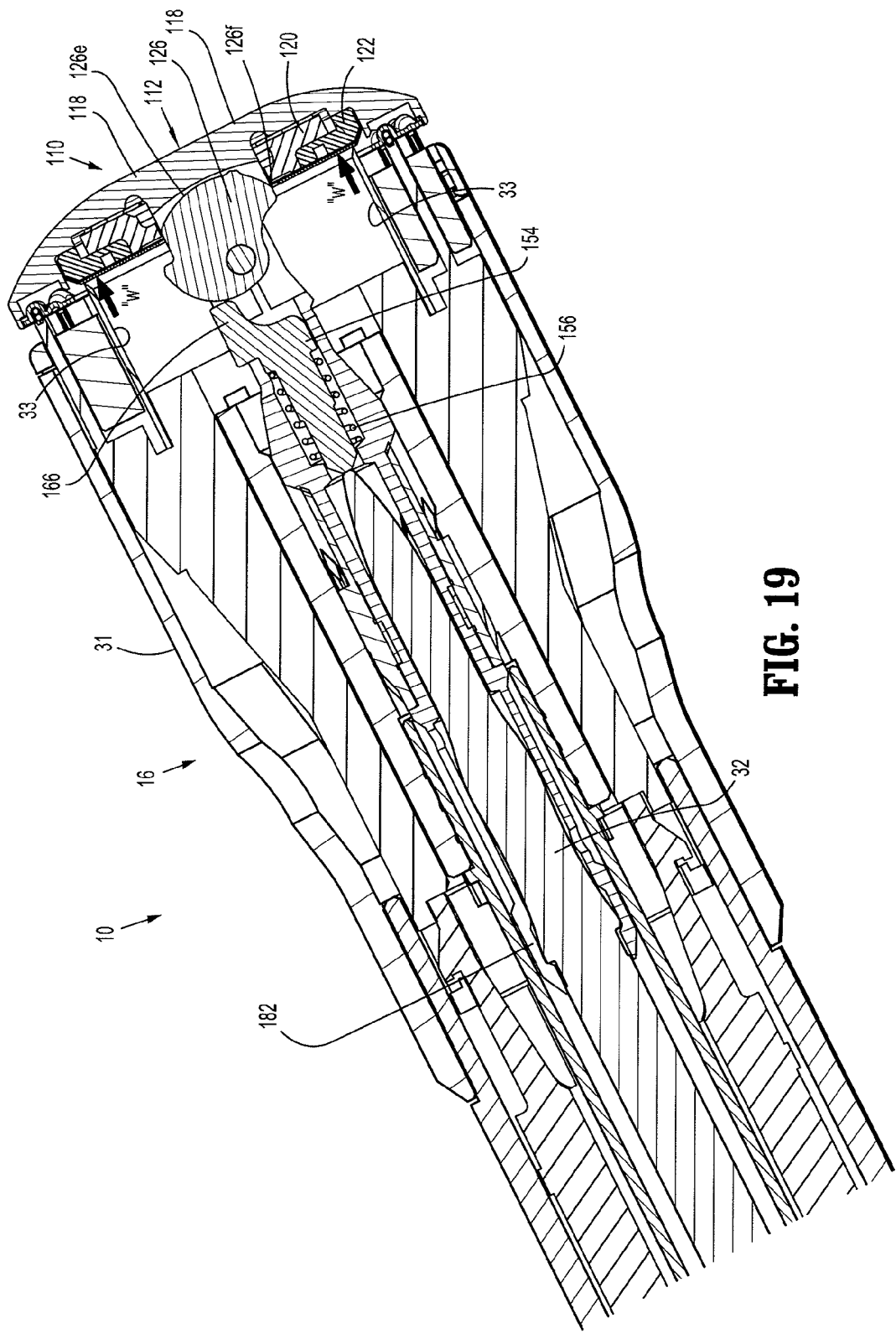
FIG. 19 is an enlarged cross-sectional side view of the distal head portion of the surgical stapling device of FIG. 1, including the connected anvil assembly of FIGS. 1-4 shown in a post-fired non-tilted operative position.
Figure 20:
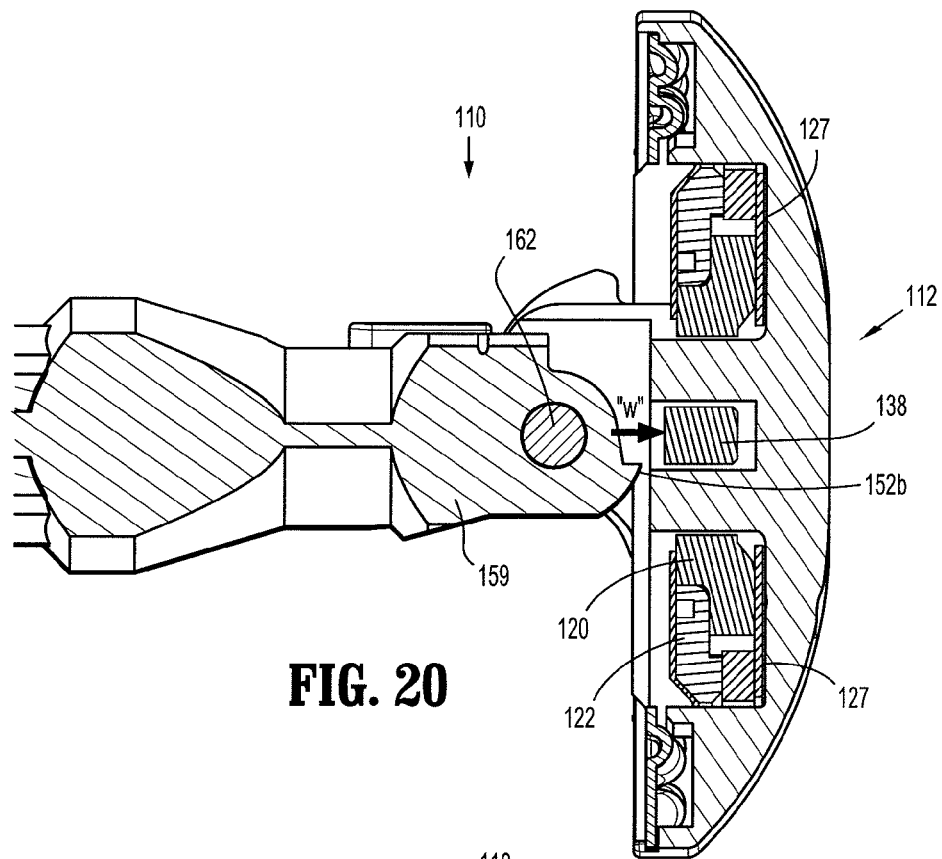
FIG. 20 is an enlarged cross-sectional side view of the distal end of the anvil assembly of FIGS. 1-4 in the post-fired non-tilted operative position corresponding to the position of FIG. 19.
Figure 21:
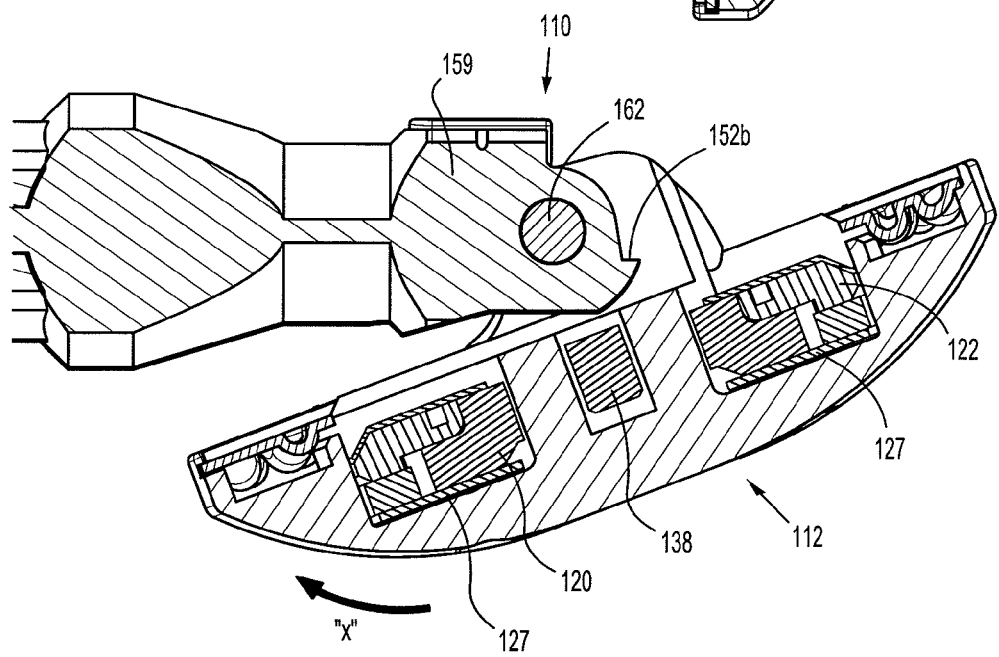
FIG. 21 is an enlarged cross-sectional side view of the distal end of the anvil assembly of FIGS. 1-4 in a post-fired second tilted position.

With reference to FIGS. 3 and 4, a second end of center rod 152 includes a bore 180 defined by a plurality of flexible arms 182. Flexible arms 182 each include an opening 182a dimensioned to receive a projection formed on or connected to a shell assembly 31 (FIG. 18). Alternatively, openings 182a may be configured to receive a suture for permitting retrieval of anvil assembly 110. The proximal ends of each of the flexible arms 182 include an internal shoulder 184 dimensioned to releasably engage shell assembly 31 of surgical stapling device 10 to secure anvil assembly 110 to the surgical stapling device. A plurality of splines 186 are formed about center rod 152. Splines 186 function to align anvil assembly 110 with the staple holding portion of a surgical stapling device. Center rod 152 also includes an annular recessed portion 190 to facilitate grasping of anvil assembly 110 by a surgeon with a grasper. Recessed portion 190 may include a roughened or knurled surface or an overmold to facilitate grasping of anvil assembly 110.

With reference now to FIGS. 9-12, a system for delivering anvil assembly 110 within a patient is shown generally as anvil delivery system 50. Anvil delivery system 50 includes a flexible tube 52 and an adapter 62. Flexible tube 52 includes an open end 52a. Adapter 62 and anvil assembly 110 are supported on open end 52a of flexible tube 52. Open end 52a of flexible tube 52 includes a throughbore 53 extending therethrough configured to receive a locking pin 54. Open end 52a further includes an opening 55, used for alignment of the printing on the tube 50 during manufacture. Closed end 52b of flexible tube 52 is configured for trans-oral insertion in a patient. Flexible tube 52 may include markings or other gradations 56 along the length thereof to indicate to a surgeon how much of flexible tube 52 has been received within the patient during insertion and/or to indicate the length of flexible tube 52 remaining in the patient during removal.

With particular reference to FIG. 10, adapter 62 includes a first end 62a configured to be received within open end 52a of flexible tube 52 and a second end 62b configured to be received within bore 180 formed in center rod 152 of anvil assembly 110. First end 62a includes a series of annular rings 64 configured to frictionally retain first end 62a of adapter 62 within open end 52a of flexible tube 52. Second end 62b of adapter 62 includes a longitudinal guide member 66 configured to be received between flexible arms 182 formed in center rod 152 of anvil assembly 110. In addition, second end 62b of adapter 62 is sized to allow center rod 152 of anvil assembly 110 to freely slide into and off second end 62b of adapter 62. Adapter 62 further includes a first throughbore 70 formed in a central hub portion 62c as well as second and third throughbores 72, 74 formed in first end 62a. Throughbore 72 is configured to align with throughbore 53 formed in open end 52a of flexible tube 52 and is sized to receive locking pin 54. Bore 74 is configured to receive both ends of the suture S1. Bore 70 can also receive the suture ends to enhance retention.

With particular reference now to FIGS. 10-14, anvil assembly 110 is supported on anvil delivery system 50. Securing anvil assembly 110 to anvil delivery system 50 requires that suture "$S_1$" is thread through openings 119a (shown also in FIG. 2) formed on anvil head 112 such that first and second ends of suture "$S_1$" are positioned on different sides of center rod 152. Second end 62b of adapter 62 is positioned within throughbore 180 of center rod 152 such that longitudinal guide 66 is received between two of arm members 182. Each of the first and second ends of suture "$S_1$" is preferably inserted through bore 74 formed in adapter 64 and through open end 52a of flexible member 52. Anvil head 112 is then rotated to a first tilted position as first and second ends of suture "$S_1$" are pulled through opening 74, applying tension on the anvil head forcing it to pivot counterclockwise as viewed in the orientation of FIG. 13. Such pivoting forces plunger 154 proximally as described above.

First end 62a of adapter 62 is inserted into open end 52a of flexible member 52. The frictional contact between annular rings 64 of first end 62a of adapter 62 and an inner surface of flexible tube 52 secures adapter 62 to flexible tube 52 and prevents suture "$S_1$" from loosening as it is clinched between the outer wall of the adapter 62 and inner wall of flexible tube 52. It is envisioned that more than one suture may be used to secure anvil head assembly 112 in a pre-fired tilted position.

It is also envisioned that the suture $S_1$ need not be passed through bore 74 but instead is just clamped between the adapter 62 and the inner wall of the flexible tube 52.

Figure 15:
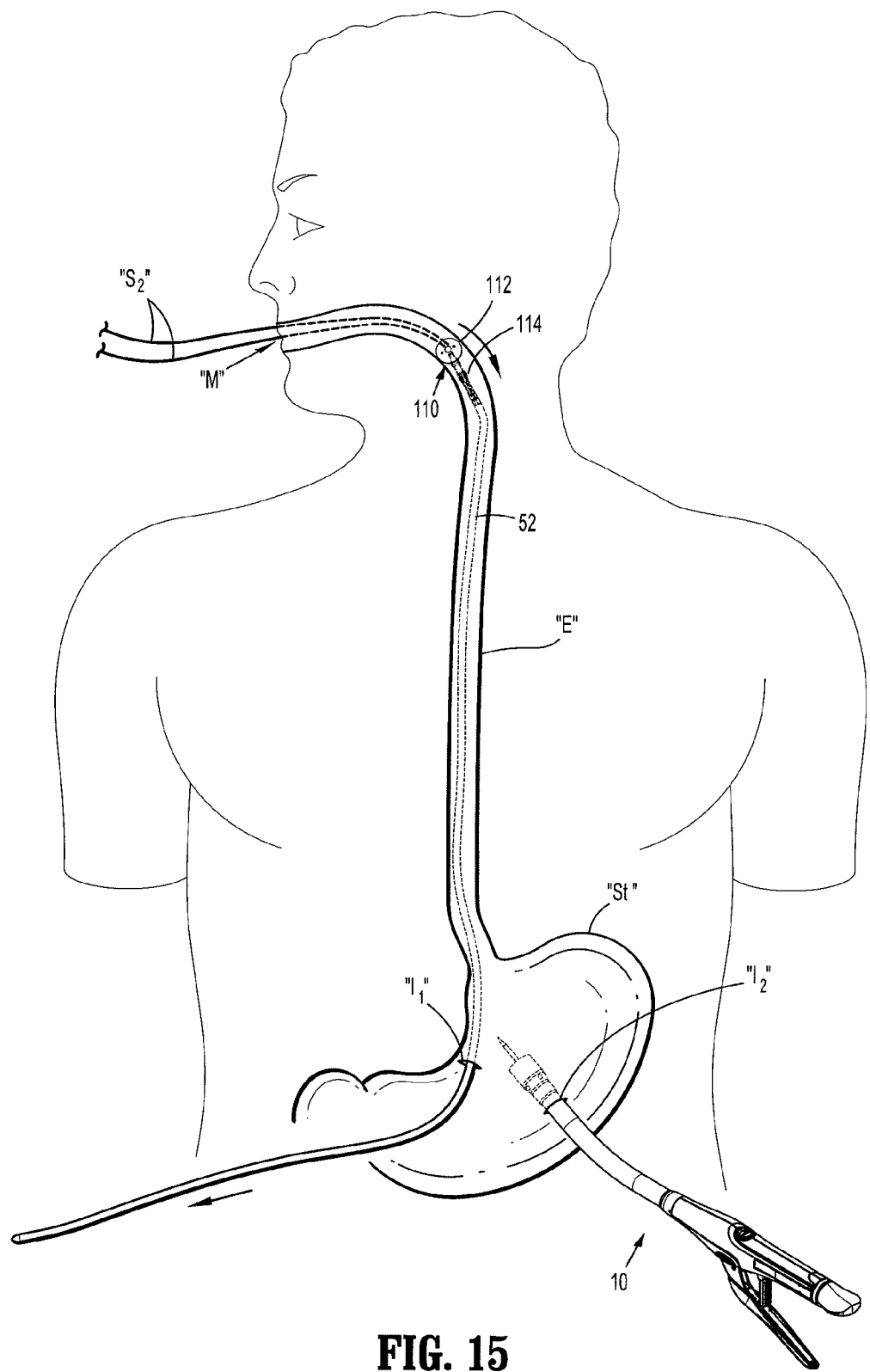
FIG. 15 is an illustration of the surgical stapling instrument of FIG. 1 and the anvil delivery system of FIG. 9 with connected anvil assembly being inserted trans-orally into a patient.

With reference now to FIG. 15, a method for delivering anvil assembly 110 to a surgical site within a patient will be described. In one preferred method, anvil assembly 110 is provided in the first tilted position supported on anvil delivery system 50 and ready for delivery. Alternatively, a clinician secures anvil assembly 110 to anvil delivery system 50 as discussed above. With anvil assembly 110 secured to flexible tube 52, the surgeon inserts closed end 52b of flexible tube 52 in the patient's mouth "M" and moves closed end 52b along with flexible tube 52 down through esophagus "E" to a surgical site, i.e., the stomach "St".

After insertion, the surgeon then makes a first incision "$I_1$" at the surgical site (stomach "St" as shown) to create an inner access to closed end 52b of flexible tube 52 and then pulls open end 52b of flexible tube 52 through first incision "$I_1$". In some procedures it may be beneficial to pull flexible tube 52 through incision "$I_1$" until center rod 152 of anvil assembly 110 advances through first incision "$I_1$". When anvil assembly 110 is properly positioned at the surgical site, the surgeon releases anvil assembly 110 from anvil delivery system 50 by cutting suture "$S_1$" and separating anvil assembly 110 from second end 62b of adapter 62. Flexible tube 52 (with fitting 62) may then be pulled from the body through first incision "$I_1$".

Severing of suture "$S_1$" permits plunger 154 to extend from within bore 164, thereby causing finger 166 to engage body portion 126c of cam latch member 126. Rotation of cam latch member 126 (clockwise as viewed in the orientation of FIG. 14) causes edge 126f of latch member 126, engaged with the inner periphery of backup plate 120, to urge anvil head assembly 112 to return to a non-tilted operative position (e.g. the position of FIG. 6). Additionally, the distal end of stapling device 10 may be configured to engage finger 166 of plunger 154 as anvil assembly 110 is attached to surgical stapling device 10. In this manner, the distal end of surgical stapling device 10 urges plunger 154 distally, thereby ensuring the rotation of cam latch 126 and anvil head assembly 112 to a non-tilted position.

With particular reference to FIG. 15, in one method, a second incision "$I_2$" is then formed at the surgical site such that distal head portion 16 of surgical stapling device 10 may be received therethrough. Alternatively, distal head portion 16 of surgical stapling device 10 may be received through first incision "$I_1$" once anvil delivery system 50 has been removed therefrom.

Figure 16:
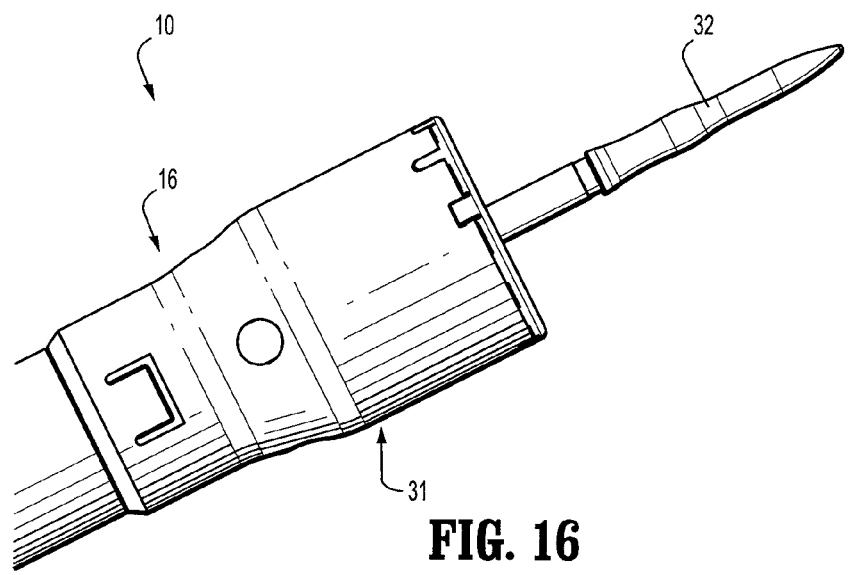
FIG. 16 is an enlarged side view of the distal head portion of the surgical stapling device of FIGS. 1 and 15.
Figure 17:
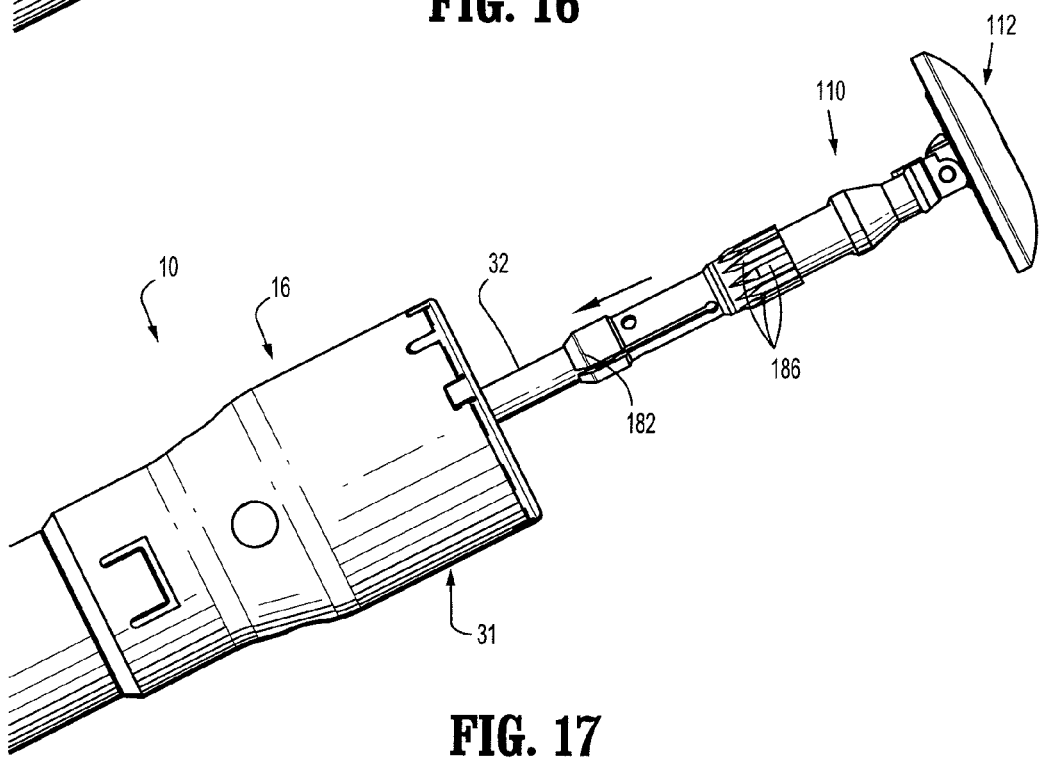
FIG. 17 is an enlarged side view of the distal head portion of the surgical stapling device of FIGS. 1 and 15, showing the anvil assembly of FIGS. 1-4 received thereon.

Turning briefly to FIGS. 16 and 17, anvil assembly 110 is operably received on an anvil retainer 32 extending from shell assembly 31 formed on a distal end of surgical stapling device 10. Once anvil assembly 110 is received on surgical stapling device 10, surgical stapling device 10 operates in the manner discussed in U.S. Pat. No. 7,364,060, previously incorporated herein in its entirety by reference. Note that alternatively, suture S1 can be severed after the distal head portion 16 of the stapling device 10 receives the anvil assembly 110. After attachment, the rotation knob 22 is rotated to approximate the anvil assembly 110 and distal head portion 16 to clamp tissue therebetween, and then the firing trigger is actuated to fires the staples as disclosed in U.S. Pat. No. 7,364,060.

The operation of anvil assembly 110 will now be described with reference to FIGS. 18-23. When anvil assembly 110 is in its pre-fired non-tilted position (e.g. FIG. 18), backup plate 120 is spaced from backwall 118a of housing 118 by retainer 127 and protrusions 152b of center rod 152 engage fingers 138 of backup plate 120 (also shown in FIGS. 6 and 7) to prevent tilting of anvil head assembly 112 about pivot member 162. Finger 166 of plunger 154 is urged by spring 156 into engagement with body portion 126c of cam latch member 126 to urge cam latch member 126 in a clockwise direction (as viewed in FIG. 18), about pivot member 162 such that edge 126f of cam latch member 126 engages inner periphery 120b of backup member 120.

Figure 22:
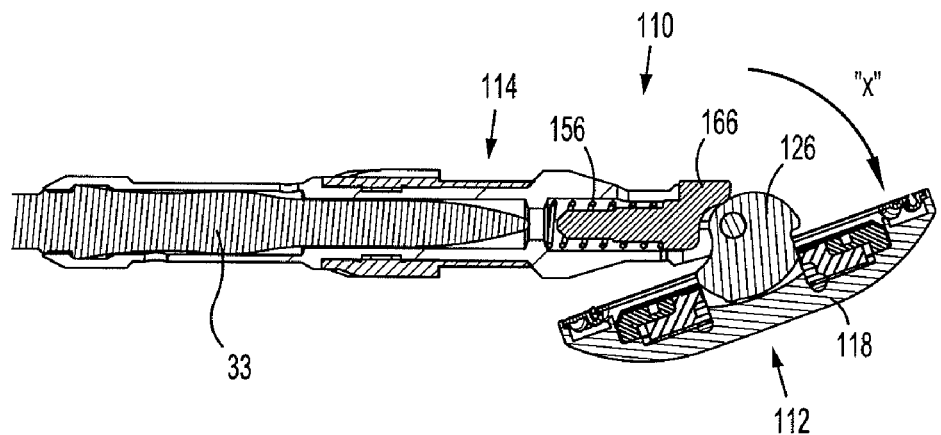
FIG. 22 is a cross-sectional side view of the anvil assembly of FIGS. 1-4 in a post-fired second tilted position (corresponding to the position of FIG. 21) shown supported on an anvil retainer of the surgical stapling device of FIG. 1.
Figure 22A:
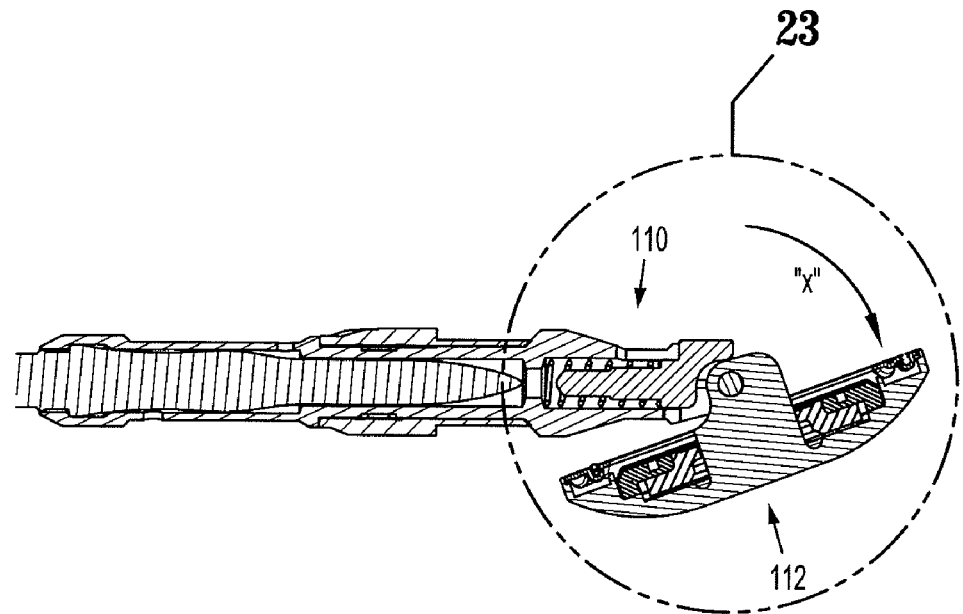
FIG. 22A is another cross-sectional side view of the anvil assembly of FIGS. 1-4 corresponding to the anvil assembly position of FIG. 22.
Figure 23:
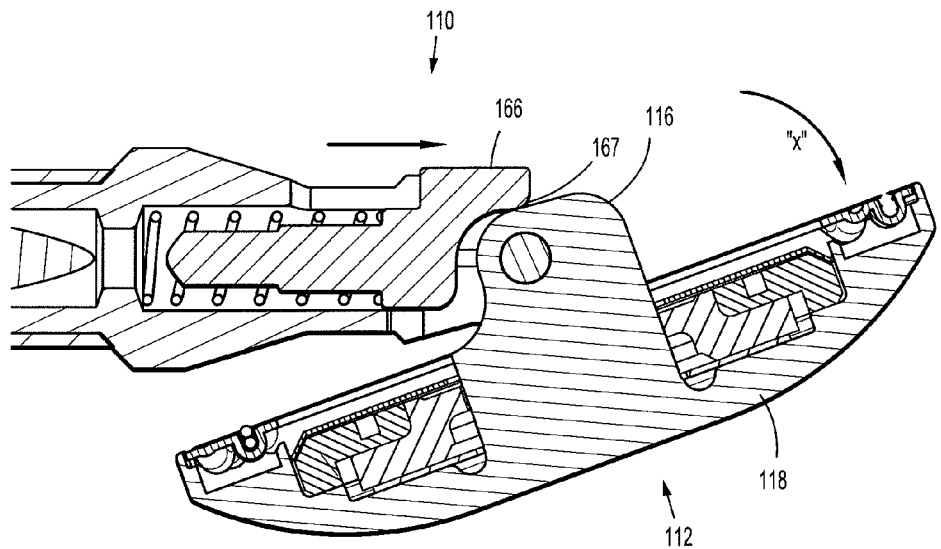
FIG. 23 is an enlarged view showing the designated area of detail of FIG. 22A.

The firing of surgical stapling device 10 causes a knife blade 33 thereof to engage cutting ring 122 to move cutting ring 122 and backup plate 120 into annular recess 136 of housing 118 of anvil head assembly 112. Arrows "W" in FIG. 19 indicate how cutting ring 122 and backup plate 120 move as a result of the firing of surgical stapling device 10. When such movement occurs, deformable tabs 127a of retainer 127 (labeled in FIGS. 6 and 7) are deformed against backwall 118a of housing 118 and fingers 138 of backup member 120 move away from protrusions 152b of center rod 152. Further, inner periphery 120b of backup plate 120 moves past edge 126f of cam latch member 126 such that cam latch member 126 is urged to pivot about pivot member 162 (clockwise as viewed in the orientation of FIG. 21) in the direction indicated by arrow "X" in FIGS. 21 and 22 by plunger 154 (spring biased distally) to a position in which body portion 126e of cam latch 126 is positioned in front of and engages backup plate 120. Engagement of plunger 154 with cam latch member 126 urges cam member 126 to further rotate clockwise which due to its configuration enables spring biased plunger 154 to move further distally so angled surface 167 of plunger 154 contacts the surface of post 116 of anvil head assembly 112 to move the anvil head assembly 118 to a second tilted position (FIGS. 22A and 23). It is noted that anvil head assembly 112 will not immediately tilt to its second tilted position upon firing of surgical stapling device 10 because, upon firing, anvil head assembly 112 is in an approximated position, i.e., the anvil head assembly 112 is in close alignment with shell assembly 31 of stapling device 10, and, therefore, does not provide room for head assembly 112 to pivot. As such, the anvil head assembly 112 will only begin to tilt when anvil assembly 110 and shell assembly 31 of surgical stapling device 10 are being unapproximated and there is a sufficient gap between the anvil assembly 110 and the distal head portion 16 of the stapling device 10.

Figure 24:
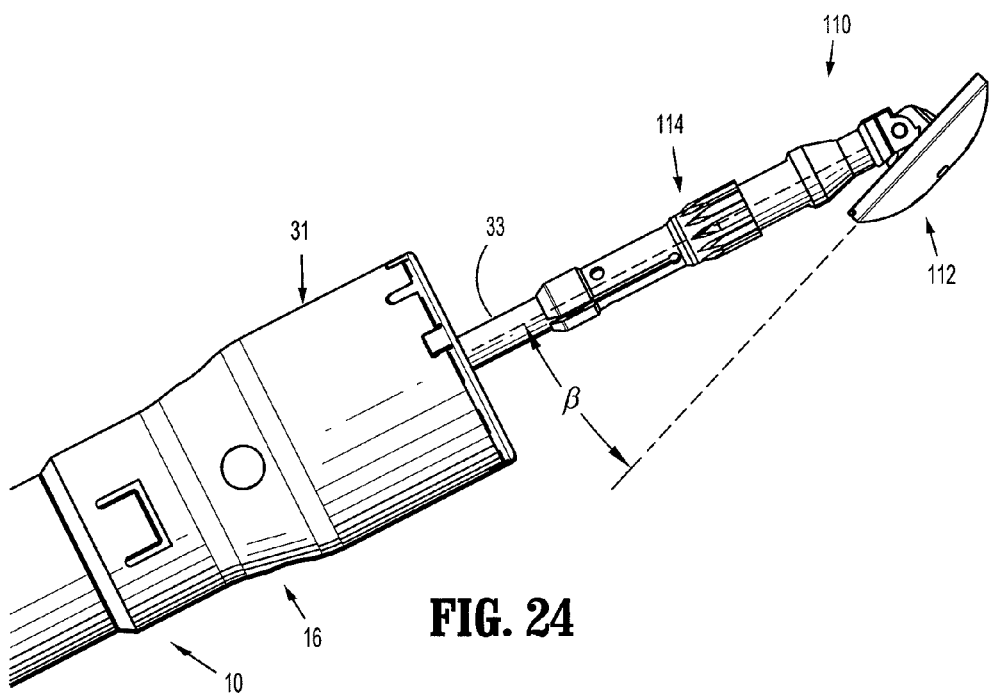
FIG. 24 is a side view of the anvil assembly of FIG. 22 supported on the anvil retainer of the surgical stapling device of FIG. 1.

As anvil head assembly 112 pivots towards its forward or second tilted position, finger 166 of plunger 154 maintains surface 126e of cam latch member 126 in contact with backup plate 120 to prevent backup plate 120 from sticking to the knife blade as the knife blade is retracted. It is noted that curved surface 126e of cam latch member is configured to eliminate any gap and ensure contact between surface 126e of cam latch member 126 and backup plate 120 to hold backup plate 120 in place during and after the knife blade is retracted such that the cutting ring and backup plate assembly stay in their correct position during continued tilting of anvil assembly 112. Anvil assembly 110 is configured such that anvil head assembly tilts to a forward or second tilted position β degrees (FIG. 24) relative to center rod assembly 114. As can be appreciated, the anvil head assembly therefore pivots in a first direction from an initial (first) tilted position to an untilted operative position for application of staples. After firing of the instrument, the anvil head pivots in the same direction to a second tilted position. In one embodiment, anvil head assembly 112 is tilted less than ninety degrees and preferably about seventy degrees (70°) to its second tilted position such that the total pivoting movement of the anvil from the retracted or first tilted position to the forward or second tilted position is about one-hundred and forty degrees (140°). It should however be noted that the tilting of anvil head assembly 112 to other degrees for the first and/or second tilted position is also contemplated.

It will be understood that various modifications may be made to the embodiments disclosed herein. For example, the cutting ring and backup plate can be unitarily or integrally formed. Further, the anvil assembly need not have cutting ring cover. Therefore, the above description should not be construed as limiting, but merely as exemplifications of preferred embodiments. Those skilled in the art will envision other modifications within the scope and spirit of the claims appended hereto.

What is claimed is:

1. A surgical tilt anvil assembly comprising:
    a rod; and
    an anvil head assembly pivotally secured to the rod and pivotal in relation to the rod in a first direction from a first tilted position for insertion to an operative position, and further pivotal in relation to the rod in the first direction from the operative position to a second tilted position for removal; and
    a plunger and a pivotal cam latch member, wherein rotation of the latch member enables distal movement of the plunger to move the head assembly from the first tilted position to the operative position.

2. A tilt anvil assembly according to claim 1, wherein the head assembly moves through an arc of about 140 degrees from the first tilted position to the second tilted position.

3. A tilt anvil assembly according to claim 1, further comprising a suture connected to the head assembly to maintain the head assembly in the first tilted position.

4. A surgical anvil delivery system comprising:
    an anvil assembly including a rod and a head assembly pivotally secured to the rod, the head assembly movable from a first tilted position to a non-tilted operative position;
    a flexible tube, the anvil assembly connected to the flexible tube;
    a tensioning member connected to the head assembly and maintaining the head assembly in the first tilted position such that release of the tensioning member returns the head assembly to the non-tilted position, wherein the tensioning member is a first suture extending through a hole in the head assembly and into an opening in the flexible tube; and
    a second suture connected to the head assembly, the second suture extending in a direction different than the first suture.

5. The anvil delivery system of claim 4, wherein the head assembly is further pivotable to a second tilted position after positioning in the operative non-tilted position, the second tilted position being different than the first tilted position.

6. The anvil delivery system of claim 4 further comprising an adapter connecting the anvil assembly to the flexible tube.

7. A surgical anvil delivery system comprising:
    an anvil assembly including a rod and a head assembly pivotally secured to the rod, the head assembly movable from a first tilted position to a non-tilted operative position;
    a flexible tube, the anvil assembly connected to the flexible tube; and
    a tensioning member connected to the head assembly and maintaining the head assembly in the first tilted position such that release of the tensioning member returns the head assembly to the non-tilted position, wherein the tensioning member is a first suture extending through a hole in the head assembly and into an opening in the flexible tube; and
    wherein the anvil assembly further includes a rotatable cam member and a plunger, the plunger spring biased into contact with the cam member and movable distally to rotate the cam member to move the head assembly from the first tilted position to the operative position.

8. The anvil delivery system of claim 7, wherein the cam member is further rotatable and the plunger is movable further distally to move the head assembly from the operative position to a second tilted position different than the first tilted position.

\* \* \* \* \*